(12) United States Patent
Tan et al.

(10) Patent No.: US 12,097,330 B2
(45) Date of Patent: Sep. 24, 2024

(54) MASSAGE APPARATUS, SYSTEM AND METHOD CAPABLE OF DERIVING A PARAMETER OF AN INDIVIDUAL

(71) Applicant: OSIM INTERNATIONAL PTE. LTD., Singapore (SG)

(72) Inventors: Kia Tong Tan, Singapore (SG); Gilbert Realuyo, Singapore (SG); Rui Zou, San Jose, CA (US); Kiran Buch, San Jose, CA (US)

(73) Assignee: OSIM INTERNATIONAL PTE. LTD., Singapore (SG)

( * ) Notice: Subject to any disclaimer, the term of this patent is extended or adjusted under 35 U.S.C. 154(b) by 927 days.

(21) Appl. No.: 17/259,954

(22) PCT Filed: Dec. 26, 2018

(86) PCT No.: PCT/SG2018/050628
§ 371 (c)(1),
(2) Date: Jan. 13, 2021

(87) PCT Pub. No.: WO2020/139189
PCT Pub. Date: Jul. 2, 2020

(65) Prior Publication Data
US 2021/0308415 A1   Oct. 7, 2021

(51) Int. Cl.
*A61M 21/02*   (2006.01)
*A61B 5/00*   (2006.01)
(Continued)

(52) U.S. Cl.
CPC .............. *A61M 21/02* (2013.01); *A61H 7/00* (2013.01); *G16H 10/60* (2018.01); *G16H 40/67* (2018.01);
(Continued)

(58) Field of Classification Search
CPC . A61M 21/02; A61M 2021/0022; A61H 7/00; A61H 2201/0149; A61H 2201/5097;
(Continued)

(56) References Cited

U.S. PATENT DOCUMENTS

2010/0249613 A1* 9/2010 Hashimoto ........... A61M 21/02
600/485
2016/0283856 A1   9/2016 Jayaraman et al.
(Continued)

FOREIGN PATENT DOCUMENTS

CN   106068097 A   11/2016
CN   106420295 A   2/2017
(Continued)

OTHER PUBLICATIONS

Notification of the First Office Action dated Feb. 3, 2023 for Chinese Patent Application No. 201880004675.X.
(Continued)

*Primary Examiner* — Thaddeus B Cox
*Assistant Examiner* — Joshua Daryl D Lannu
(74) *Attorney, Agent, or Firm* — JCIP; Joseph G. Chu; Jeremy I. Maynard (57) ABSTRACT

Disclosed is a massage apparatus including a processor configurable to receive a first dataset associated with a physiological parameter of an individual to derive a first emotional indication of the individual; wherein the first emotional indication and the first dataset are configured as inputs to derive a second emotional indication of the individual.

20 Claims, 4 Drawing Sheets

(51) Int. Cl.

| | |
|---|---|
| *A61B 5/0205* | (2006.01) |
| *A61B 5/332* | (2021.01) |
| *A61F 7/00* | (2006.01) |
| *A61H 7/00* | (2006.01) |
| *A61H 23/00* | (2006.01) |
| *A61M 21/00* | (2006.01) |
| *G16H 10/60* | (2018.01) |
| *G16H 40/67* | (2018.01) |
| *G16H 50/30* | (2018.01) |

(52) U.S. Cl.
CPC ..... *G16H 50/30* (2018.01); *A61H 2201/0149* (2013.01); *A61H 2201/5097* (2013.01); *A61H 2230/065* (2013.01); *A61H 2230/425* (2013.01); *A61M 2021/0022* (2013.01)

(58) Field of Classification Search
CPC ........ A61H 2230/065; A61H 2230/425; A61H 2201/0221; A61H 7/007; A61H 23/00; A61H 2201/1633; A61H 2201/5058; A61H 2203/0431; A61H 2230/04; A61H 2230/30; A61H 2230/505; A61H 9/0071; A61H 9/0078; A61H 15/0078; A61H 23/006; A61H 2201/5041; G16H 10/60; G16H 40/67; G16H 50/30; A61B 5/332; A61B 5/02055; A61B 5/6891; A61B 5/02405; A61B 5/0816; A61B 5/4848; A61B 5/6898; A61B 5/165; A61B 5/0205; A61B 5/0245; A61B 5/4836; A61F 7/007; A61F 2007/0093; A61F 2007/0095

See application file for complete search history.

(56) References Cited

U.S. PATENT DOCUMENTS

| | | | |
|---|---|---|---|
| 2017/0319122 A1* | 11/2017 | Wild | .............. G06Q 50/22 |
| 2018/0140798 A1 | 5/2018 | Tomiyama et al. | |
| 2020/0085673 A1 | 3/2020 | Seo et al. | |

FOREIGN PATENT DOCUMENTS

| | | | |
|---|---|---|---|
| CN | 207785632 U | | 8/2018 |
| CN | 110740682 A | | 1/2020 |
| JP | 2010234000 A | * | 10/2010 |
| KR | 1020170117019 A | | 10/2017 |
| KR | 1020210000248 A | | 1/2021 |

OTHER PUBLICATIONS

Search Report of Taiwan Patent Application No. 109115916.
International Search Report and Written Opinion of International Searching Authority for International Application No. PCT/SG2018/050628.
Office Action from Korean Intellectual Property Office dated Mar. 31, 2023 for Korean Application No. 10-2021-7003662.
Office Action from Korean Intellectual Property Office dated Jan. 15, 2024 for Korean Application No. 10-2021-7003662.

* cited by examiner

|  | t-test p value | before massage mean ± std | after massage mean ± std |
|---|---|---|---|
| Heart Rate | 0.0048 | 67.44 ± 11.94 | 65.12 ± 10.06 |
| Respiration Rate | 0.0093 | 15.23 ± 2.95 | 14.54 ± 2.57 |
| Stress | 0.00058 | 2.16 ± 0.96 | 1.96 ± 0.82 |

Figure. 3

| Score | Interpretation |
|---|---|
| 1-20 | Calm |
| 21-40 | Relaxed |
| 41-60 | Balanced |
| 61-80 | Motivated |
| 81-100 | Agitated/Anxiety/Excited |

Figure. 4

MASSAGE APPARATUS, SYSTEM AND METHOD CAPABLE OF DERIVING A PARAMETER OF AN INDIVIDUAL

FIELD

The present disclosure relates generally to massage apparatus, system and method capable of deriving one or more physiological and/or emotional parameters of an individual.

BACKGROUND

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

Massage apparatus or devices, such as massage chairs, have been gaining popularity as a lifestyle equipment. Besides having massage mechanisms or drives capable of providing massage functions to different parts of a body, some massage devices may include sensors or measurement devices to obtain physiological parameters such as heart rate, respiratory rate, temperature, and/or blood pressure etc. of an individual. For example, in the case of a massage chair, physiological parameters may be obtained when the individual is seated on the massage chair.

While physiological parameters are useful, there exists a need to provide a more comprehensive measurement of the indicators which can affect the well-being of individuals.

It is an object to meet the aforementioned need at least in part.

SUMMARY

A system and/or massage apparatus incorporating one or more physiological sensors to obtain a plurality of physiological parameters of an individual, and thereafter derive a first emotional function associated with the plurality of physiological parameters is disclosed.

In some embodiments, the plurality of physiological parameters includes heart rate and respiration rate of the individual.

In some embodiments, a second emotional indication is derived based on the plurality of physiological parameters and the first emotional indication.

In some embodiments, the second emotional function is an indication of a state where the individual experiences a body tension. The body tension can be quantified by a mathematical function expressed as:—

$$\text{Body Tension} = A * \text{Heart Rate} + B * \text{Respiration Rate} + C * \text{Stress}$$

wherein A, B and C are non-zero weights associated with heart rate, respiration rate and a stress level of the individual respectively.

In some embodiments, A, B and C are positive values.

In some embodiments, the non-zero weights A, B, and C are calculated based on an averaged heart rate, an average respiration rate, and an average stress value.

In some embodiments, the non-zero weight A is computed based on an average heart rate range of 33 to 200 beats per minute, which corresponds to a value of A between 0.16 and 1.11.

In some embodiments, the non-zero weight B is computed based on an average respiration rate of 8 to 25 breaths per minute, which corresponds to a value of B between 1.33 and 4.16.

In some embodiments, the non-zero weight C is computed based on an average stress value of 1 to 5, which corresponds to a value of C between 6.66 and 33.33.

In some embodiments, the weights A, B and C can be calibrated based on physiological data of an individual collected over a predetermined period.

In some embodiments, the weights A, B and C can be calibrated based on physiological data of a group of individuals collected over a predetermined period.

In some embodiments, the sensors may be positioned on the massage apparatus. These may include electrodes configured as plates on the surface of the massage apparatus to detect the heart rate of the individual.

In some embodiments, the sensors may be positioned on a wearable device to detect at least one physiological parameter of the individual. The wearable device may include a watch.

According to an aspect of the present disclosure there is a massage apparatus having a processor configurable to receive a first dataset associated with a physiological parameter of an individual to derive a first emotional indication of the individual, wherein the first emotional indication and the first dataset are arranged as inputs to derive a second emotional indication of the individual.

In some embodiments, the first emotional indication is a stress level of the individual and the second emotional indication is a tension level of the individual.

In some embodiments, the massage apparatus includes a communication module configured to receive or send the first dataset.

In some embodiments, the communication module is a wireless communication module.

In some embodiments, a third emotional indication of a mood of the individual may be derived. The mood can be derived based on a heart rate measurement of the individual for a predetermined period. The predetermined period should be at least 30 seconds and preferably one minute duration. The heart rate signal can be obtained via an ECG (Electrocardiography) method.

The mood of the individual can preferably be derived based on a HRV (Heart Rate Variability) value calculated from the heart rate signal. HRV represents the time difference between successive heart beats. Frequency components of the HRV signal are then analysed to compute a value from 1 to 100 indicative of the mood of the individual.

In some embodiments, the frequency components of the HRV signal include a first frequency component from 0.15 Hz to 0.4 Hz and a second frequency component from 0.04 Hz to 0.15 Hz. The first frequency HRV component is relatively higher and has been linked to parasympathetic activity in the autonomic nervous system (ANS). The second frequency HRV (i.e. the lower frequency HRV), is linked to sympathetic activity in the ANS.

In some embodiments the massage apparatus is a massage chair.

In some embodiments one or more massage drives of the massage chair is arranged to receive the physiological parameter, the first emotional indication, the second emotional indication and/or the third emotional indication of the individual as feedback data to actuate, de-actuate, accelerate or decelerate the one or more massage drives.

According to another aspect of the present disclosure there is a method of deriving a parameter of an individual including the steps of:—(a.) receiving a first dataset associated with a physiological parameter of an individual to derive a first emotional indication of the individual; (b.) arranging the first emotional indication and the first dataset as inputs to derive a second emotional indication of the individual.

According to another aspect of the disclosure there is a non-transitory computer readable medium storing executable computer instructions such that when executed causes a computer to execute a method of deriving a parameter of an individual including the steps of:—(a.) receiving a first dataset associated with a physiological parameter of an individual to derive a first emotional indication of the individual; (b.) arranging the first emotional indication and the first dataset as inputs to derive a second emotional indication of the individual.

In some embodiments, the non-transitory computer readable medium is installed in a massage apparatus. In other embodiments, the non-transitory computer readable medium is installed in a mobile device.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of non-limiting examples only, embodiments of the present invention.

DETAILED DESCRIPTION

Throughout this document, unless otherwise indicated to the contrary, the terms "comprising", "consisting of", "having" and the like, are to be construed as non-exhaustive, or in other words, as meaning "including, but not limited to".

Furthermore, throughout the document, unless the context requires otherwise, the word "include" or variations such as "includes" or "including" will be understood to imply the inclusion of a stated integer or group of integers but not the exclusion of any other integer or group of integers.

Throughout the description, it is to be appreciated that the term 'processor' and its plural form include microcontrollers, microprocessors, programmable integrated circuit chips such as application specific integrated circuit chip (ASIC), computer servers, electronic devices, and/or combination thereof capable of processing one or more input electronic signals to produce one or more output electronic signals.

Throughout the description, it is to be appreciated that the term 'emotional indication' can broadly include mental states of a user and can include stress level, mood, and/or general feelings of anxiety, pressure, well-being, relaxation etc.

Unless defined otherwise, all other technical and scientific terms used herein have the same meaning as is commonly understood by a skilled person to which the subject matter herein belongs.

According to an aspect of the disclosure there is a massage apparatus having a processor configurable to receive a first dataset associated with a physiological parameter of an individual to derive a first emotional indication of the individual, wherein the first emotional indication and the first dataset are further configured as inputs to derive a second emotional indication of the individual.

Figure 1:
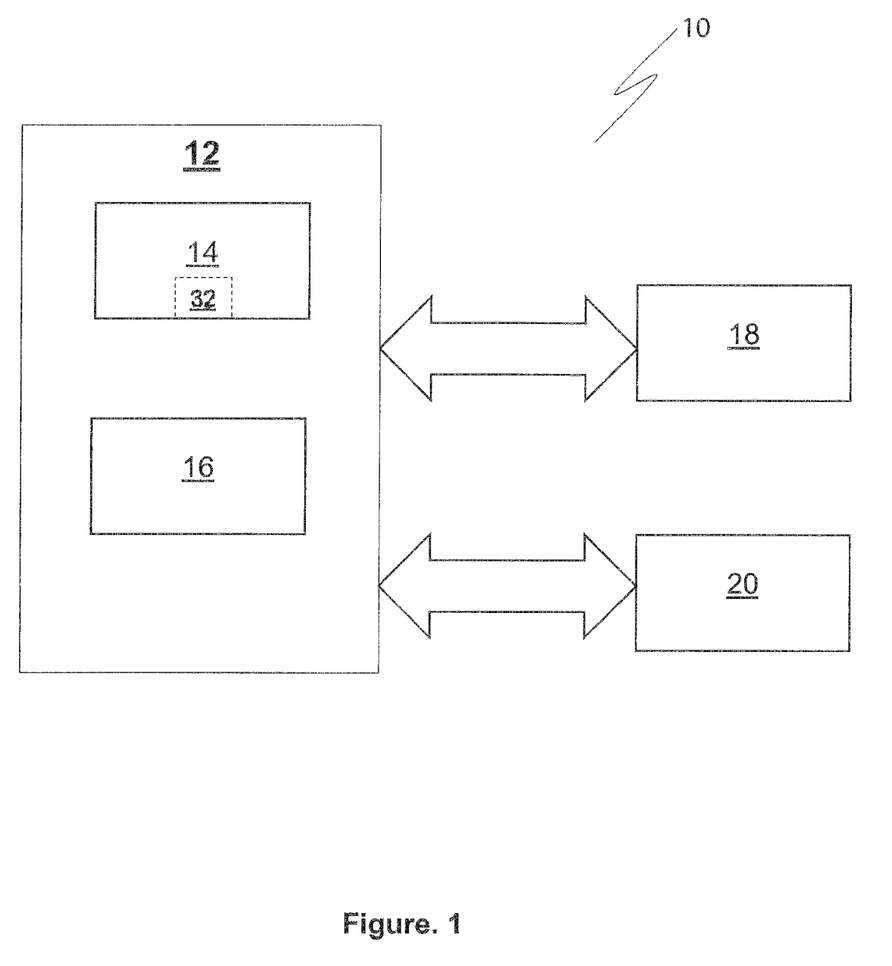
FIG. 1: illustrates an embodiment with a massage apparatus incorporating or integrating one or more physiological sensors.

FIG. 1 shows a system diagram of the massage apparatus 10 and selected features capable of sending and receiving physiological data and processing such physiological data to derive emotional indication of a user.

The massage apparatus 10 includes a processor 12, a database 14 and a communication module 16. The processor 12 may be arranged in data communication with various massage drives 18 to send control signals to the massage drives 18, or receive data such as position or drive power data from each massage drive 18.

The massage apparatus 10 includes a physiological sensor 20 for detecting or calculating a physiological parameter of a user. In some embodiments, the physiological sensor 20 is a heart rate sensor arranged to detect the heart rate of a user using the massage apparatus 10. In some embodiments the heart rate sensor may be an electrocardiography (ECG) sensor capable of obtaining ECG related information from the user. It is appreciable that the ECG related information may be obtained whether or not the user is undergoing massage. In some embodiments, the ECG information may be obtained before a user undergoes a massage sequence and after the user undergoes the massage sequence. The obtained ECG information before and after the massage sequence may be analysed as a possible way to measure the efficacy of the massage sequence.

In some embodiments, the ECG information may be obtained while the individual is undergoing massage.

The ECG related information can include heart rate variability (HRV) and ECG derived respiratory (EDR) signal per cardiac cycle. In some embodiments, the massage apparatus 10 further includes one or more additional sensors for deriving the respiration rate of the user of the massage apparatus 10.

In some embodiments, the HRV related information includes one or more of the following:—RRI, SDNN, NN50, PNN50, RMSSD, Triangular Index, HF and LF, ratio of HF to LF.

In some embodiments, a heart age index or value of the individual may be derived based on the ECG information. Other physiological or emotional parameters derived from the ECG information can include a stress indicator, heart rate and mood of the individual.

Examples of massage drives 18 include (but are not limited to) one or more rollers for kneading and tapping actions, one or more z-axis positioning mechanisms, one or more airbag pumps, one or more vibrating plate mechanisms, one or more forward positioning mechanisms and one or more heating elements.

Other examples of the massage drives 18 may include temperature regulator(s) such as heaters or coolers to provide user with a desired temperature when massaging.

The obtained physiological parameter may be organized and stored as a dataset 32. The dataset 32 is processed to derive a first emotional indication of the user. The first emotional indication may be a stress level of the user. In some embodiments, the dataset 32 may be used to derive another emotional indication such as mood of the user.

The derivation of the emotional indication-stress of the user may include the use of the ECG data.

The dataset 32, and the first emotional indication of the user such as stress may be used to derive a second emotional indication of the user. The second emotional indication may be an indication of tension experienced by the user. The relationship between the first emotional indication, second emotional indication, and physiological parameter may be expressed in the form of:—

$$\text{Body Tension} = A * \text{Heart Rate} + B * \text{Respiration Rate} + C * \text{Stress} \quad (1)$$

A, B and C are non-zero weights associated with heart rate, respiration rate and stress of the individual respectively.

A, B and C may be positive values, and may or may not be integers.

In some embodiments, the non-zero weights A, B, and C are derived based on an averaged heart rate, an average respiration rate, and an average stress value.

In some embodiments, the non-zero weight A is computed based on an average heart rate range of 33 to 200 beats per minute, which corresponds to a value of A between 0.16 and 1.11.

In some embodiments, the non-zero weight B is computed based on an average respiration rate of 8 to 25 breaths per minute, which corresponds to a value of B between 1.33 and 4.16.

In some embodiments, the non-zero weight C is computed based on an average stress value of 1 to 5, which corresponds to a value of C between 6.66 and 33.33.

In some embodiments, the weights A, B and C can be calibrated based on physiological data of an individual collected over a predetermined period, such as over a plurality of message sequences, where the physiological data is collected before and after each message sequence.

In some embodiments, the weights A, B and C can be calibrated based on physiological data of a group of individuals collected over a predetermined period. The physiological data of each individual in the group may be collected over a predetermined period, such as over a plurality of message sequences, where the physiological data of each individual in the group is collected before and after each message sequence. The group may be based on age group, gender, body weight or other biological classification.

It is appreciable that in general the non-zero weights A, B, and C can be calibrated according to individual users' baselines, also referred to as individual calibration, and can be calibrated according to a large group's states, also referred to as group calibration.

Figure 2:
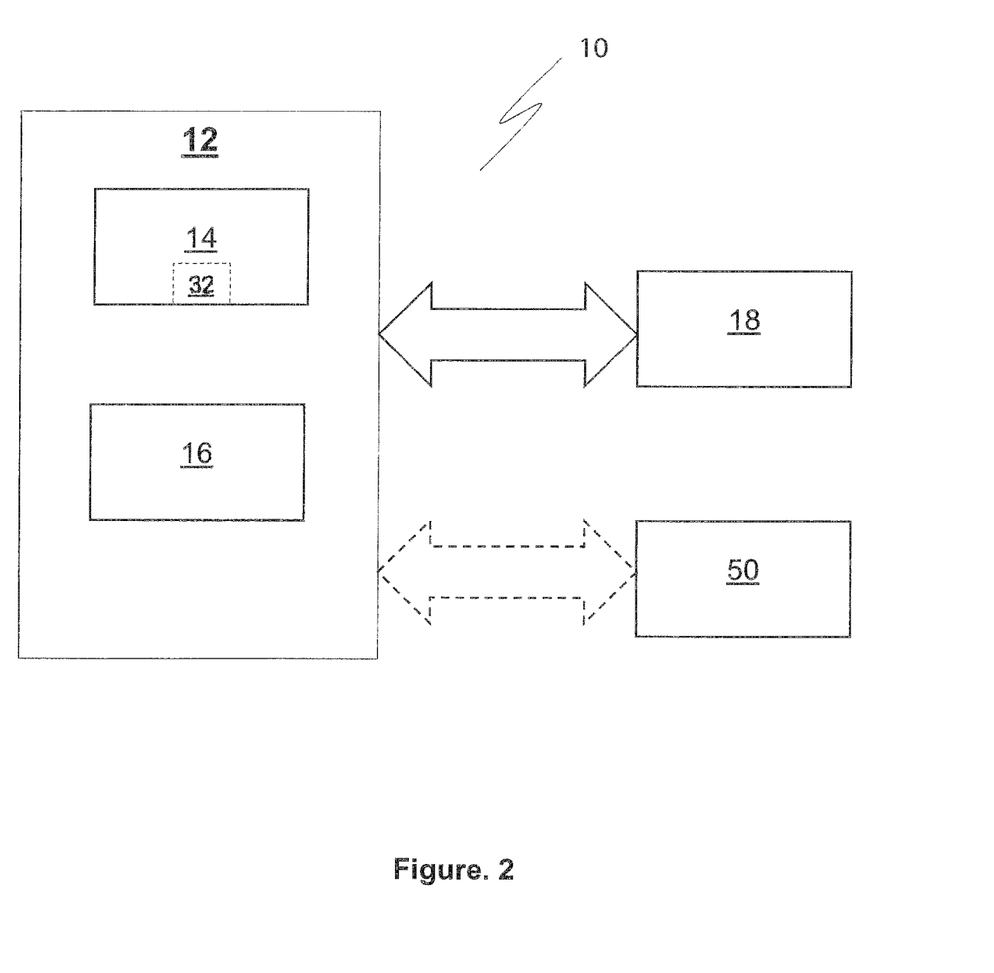
FIG. 2: illustrates another embodiment where the massage apparatus is arranged in signal communication with one or more physiological sensors.

FIG. 2 illustrates another possible embodiment where the massage apparatus 10 is arranged in data or signal communication with a wearable or mobile device 50 such as a smart watch, or a smart phone. The wearable or mobile device 50 can communicate with the massage apparatus 10 via wireless communication protocol such as Bluetooth (including the low energy or LE version) or Wi-Fi. In this embodiment, physiological data collected by the wearable or mobile device 50 may be downloaded or synchronized with the database 14. Such data may be organised as the dataset 32 (which can also be referred to as the first dataset).

The described massage apparatus 10 may be in the form a massage chair. It is appreciable that the massage chair may include sensors to detect various status and/or operating conditions of the massage drives 18. Such sensors may include, but are not limited to, a position sensor, a movement sensor, a speed sensor, a temperature sensor, a pressure sensor etc. These sensors work in tandem to detect the change in states of the drive or massage drives 18.

The massage apparatus 10 as illustrated will be described in the context of its operation, where a user utilizes the massage apparatus 10. Where the massage apparatus 10 is in the form of a massage chair, the physiological sensors may be in the form of metallic plates positioned at a pair of arm rests to obtain heart rate information of a user. Alternatively or in conjunction, the user may also be wearing wearable device 50 to obtain physiological information.

When a user is seated on the massage chair, the physiological sensors are activated to obtain heart rate data on a real time or near real time basis. The collected physiological data are stored in database 14 and organised as a dataset associated with the user. The processor 12 operates to receive the dataset to derive the respiration rate and the stress indicator of the user. The physiological sensors may be programmed to automatically obtain physiological data before a massage sequence is activated and/or after a massage sequence is completed.

The processor 12 next derives the body tension of the user in accordance with equation (1).

In some embodiments, the values of weights A, B and C may be A=0.505, B=2.222, C=16.678. These values provide for an equal contribution of each of heart rate, respiration rate and stress respectively.

Equation (1) may be derived by having ECG and respiration level data obtained from subjects (both males and females) before and after using the massage apparatus for one or more predetermined durations. In addition, each subject may be required to fill up a questionnaire describing the massage experience.

Figure 3:
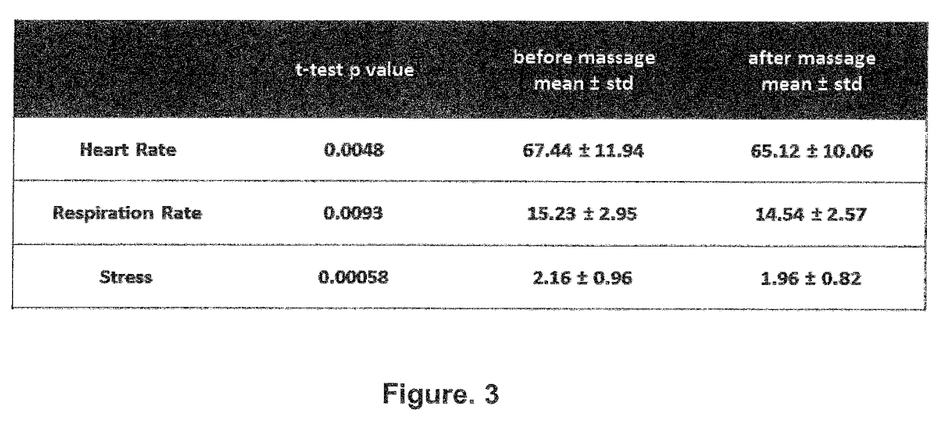
FIG. 3: illustrates experimental results demonstrating noticeable correlation between two physiological parameters and an emotional indicator with respect to one or more massage sessions.

FIG. 3 shows paired t-test results indicating that three parameters, heart rate, respiration rate and stress, amongst other parameters recorded, demonstrated significant decreases after massage sessions. The methodology used for the aforementioned conclusion is based on comparing each recorded parameter before and after massage on the same subjects and identifying any parameter with statistically significant difference.

In some embodiments, one or more other emotional indications of the user may be derived from the physiological data. An example of another emotional indication that can be derived is the mood of the user. This may be shown in FIG. 4.

Figure 4:
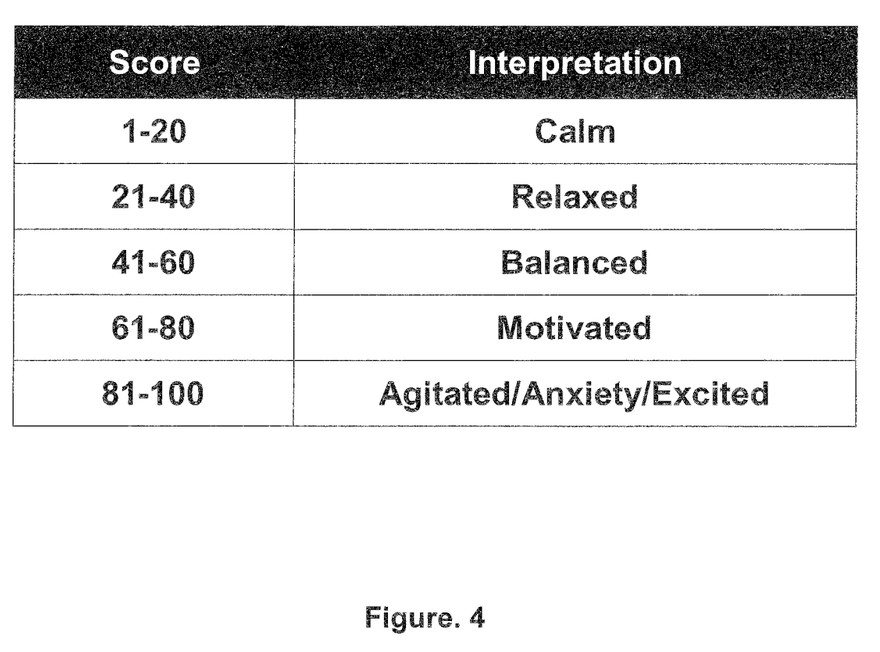
FIG. 4: shows another possible emotional indicator (mood) that can be derive from one or more physiological parameters.

The correlation in FIG. 4 may be derived based on analyzing the user's ECG measurement over a period of time. The measurement period can be at least 30 seconds and preferably one minute or more. An HRV (Heart Rate Variability) value is calculated from the ECG signal. The frequency components of the HRV signal are analyzed to compute a value from 1 to 100. An appropriate interpretation of the value can then be displayed the appropriate interpretation of the value to the user. The user's heart rate and HRV are controlled by a combination of Sympathetic and Parasympathetic components of the person's Autonomic Nervous System (ANS). The relationship between a high frequency heart rate variability (HRV) (defined from 0.15 Hz to 0.4 Hz) and a low frequency HRV (defined from 0.04 Hz to 0.15 Hz) can be calculated. High frequency HRV has been linked to parasympathetic activity in the autonomic nervous system (ANS) and low frequency HRV is linked to sympathetic activity in the ANS. Parasympathetic activity is associated by some researchers with relaxation, and sympathetic activity with tension.

In some embodiments, a "Mood" level ranging from 1 to 100 can be calibrated as shown in FIG. 4. High values of mood level tend to indicate stress or fatigue or "tense/wired" mood and low values tend to indicate being in a relaxed/calm state.

In some embodiments, a relaxation level may be derived based on the 'mood' level mathematically expressed as:

$$\text{Relaxation} = 100 - \text{Mood value} \quad (2)$$

The mood value may be based on empirical limits for HF/LF ratio of HRV mapped linearly to a value between 0 and 100.

It should be further appreciated by the person skilled in the art that variations and combinations of features described above, not being alternatives or substitutes, may be combined to form yet further embodiments falling within the intended scope of the invention.

As would be understood by a person skilled in the art, each embodiment, may be used in combination with other embodiment or several embodiments.

The invention claimed is:

1. A massage apparatus including:
   a processor configurable to
   receive a first dataset associated with a heart rate and a respiration rate of an individual obtained over a predetermined period;
   derive a stress level and a mood of the individual based on the first dataset; and
   derive a body tension indicator of the individual, the body tension indicator being quantified by a mathematical function expressed as:

$$\text{Body Tension} = A*\text{Heart Rate} + B*\text{Respiration Rate} + C*\text{Stress Level};$$

wherein A, B and C are non-zero weights associated with the heart rate, the respiration rate and the stress level of the individual respectively; and
   one or more massage drives arranged in data communication with the processor,
   wherein the one or more massage drives is arranged to receive the heart rate, the stress level, the body tension indicator and/or the mood of the individual as feedback data, and in response to the feedback data to actuate, de-actuate, accelerate or decelerate the one or more massage drives.

2. The massage apparatus of claim 1, wherein the non-zero weights A, B, and C are calculated based on an average heart rate, an average respiration rate, and an average stress value, respectively.

3. The massage apparatus of claim 2, wherein at least one of the average heart rate, the average respiration rate, and the average stress value is either a group average or an individual average.

4. The massage apparatus of claim 1, further comprising at least one physiological sensor arranged in signal or data communication with the processor to provide the first dataset associated with the heart rate and the respiration rate of the individual.

5. The massage apparatus of claim 4, wherein the at least one physiological sensor is positioned on the massage apparatus.

6. The massage apparatus of claim 4, wherein the at least one physiological sensor is positioned on a wearable device to detect the heart rate and the respiration rate of the individual.

7. The massage apparatus of claim 1, further including a communication module configured to receive or send the first dataset, wherein the communication module is a wireless protocol.

8. The massage apparatus of claim 7, wherein the communication module is a wireless communication module.

9. The massage apparatus of claim 1, wherein the heart rate of the individual obtained over the predetermined period comprises a heart rate signal and the mood of the individual is derived from a heart rate variability (HRV) value calculated from the heart rate signal.

10. The massage apparatus of claim 9, wherein the HRV value comprises frequency components that are analyzed to compute a value from 1 to 100 indicative of the mood of the individual.

11. The massage apparatus of claim 1, wherein the mood comprises a mood level which is utilized to derive a relaxation level.

12. The massage apparatus of claim 1, wherein the massage apparatus is a massage chair.

13. The massage apparatus of claim 1, wherein the non-zero weights A, B, C are calibrated based on physiological data of the individual collected over a predetermined period, wherein the predetermined period comprises a plurality of message sequences, where the physiological data is collected before and after each message sequence.

14. The massage apparatus of claim 13, wherein the non-zero weights A, B, and C are calibrated according to the individual's baselines.

15. The massage apparatus of claim 1, wherein the non-zero weights A, B and C comprise one or more of: a value of A between 0.16 and 1.11, a value of B between 1.33 and 4.16, and a value of C between 6.66 and 33.33.

16. The massage apparatus of claim 15, wherein the values of the non-zero weights A, B and C provide for an equal contribution of each of heart rate, respiration rate and stress level respectively.

17. A method for deriving a parameter of an individual using a massage apparatus including the steps of:—
   (a.) receiving a first dataset associated with a heart rate and a respiration rate of an individual obtained over a predetermined period to derive a stress level and a mood of the individual;
   (b.) arranging the stress level and the first dataset as inputs to derive a body tension indicator of the individual, the body tension indicator being quantified by a mathematical function expressed as:

$$\text{Body Tension} = A*\text{Heart Rate} + B*\text{Respiration Rate} + C*\text{Stress Level};$$

wherein A, B and C are non-zero weights associated with the heart rate, the respiration rate and the stress level of the individual respectively;
   (c.) arranging the heart rate, the stress level, the body tension indicator and/or the mood of the individual as feedback data, and in response to the feedback data, actuating, de-actuating, accelerating or decelerating one or more massage drives.

18. A non-transitory computer readable medium storing executable computer instructions such that when executed causes a computer to execute a method of deriving a parameter of an individual including the steps of:—
   (a.) receiving a first dataset associated with a heart rate and a respiration rate of an individual obtained over a predetermined period to derive a stress level and a mood of the individual;

(b.) arranging the stress level and the first dataset as inputs to derive a body tension indicator of the individual, the body tension indicator being quantified by a mathematical function expressed as:

Body Tension=$A$*Heart Rate+$B$*Respiration Rate+$C$*Stress Level;

wherein A, B and C are non-zero weights associated with the heart rate, the respiration rate and the stress level of the individual respectively;

(c.) arranging the heart rate, the stress level, the body tension indicator and/or the mood of the individual as feedback data, and in response to the feedback data, actuating, de-actuating, accelerating or decelerating one or more massage drives.

19. The non-transitory computer readable medium of claim 18, wherein the non-transitory computer readable medium is installed in a massage apparatus.

20. The non-transitory computer readable medium of claim 18, wherein the non-transitory computer readable medium is installed in a mobile device.

* * * * *